(12) United States Patent
Menys et al.

(10) Patent No.: US 12,217,428 B2
(45) Date of Patent: Feb. 4, 2025

(54) MOTION ANALYSIS OF THE DIGESTIVE TRACT

(71) Applicant: MOTILENT LIMITED, London (GB)

(72) Inventors: Alexander Menys, London (GB); Thomas S. Robbins, London (GB)

(73) Assignee: Motilent Limited, London (GB)

( * ) Notice: Subject to any disclaimer, the term of this patent is extended or adjusted under 35 U.S.C. 154(b) by 562 days.

(21) Appl. No.: 17/477,867

(22) Filed: Sep. 17, 2021

(65) Prior Publication Data

US 2022/0084207 A1 Mar. 17, 2022

Related U.S. Application Data

(60) Provisional application No. 63/079,825, filed on Sep. 17, 2020.

(51) Int. Cl.
| | |
|---|---|
| *G06T 7/00* | (2017.01) |
| *A61B 8/08* | (2006.01) |
| *G06T 7/246* | (2017.01) |
| *G06T 7/269* | (2017.01) |
| *G16H 30/20* | (2018.01) |
| *G16H 30/40* | (2018.01) |

(52) U.S. Cl.
CPC .............. *G06T 7/0016* (2013.01); *A61B 8/08* (2013.01); *A61B 8/5223* (2013.01); *G06T 7/248* (2017.01); *G06T 7/269* (2017.01); *G16H 30/20* (2018.01); *G16H 30/40* (2018.01); *G06T 2207/10132* (2013.01); *G06T 2207/30092* (2013.01)

(58) Field of Classification Search
CPC ....... G06T 7/0016; G06T 7/248; G06T 7/269; G06T 2207/10132; G06T 2207/30092; A61B 8/08; A61B 8/5223; A61B 8/463; G16H 30/20; G16H 30/40; G16H 50/20
See application file for complete search history.

(56) References Cited

U.S. PATENT DOCUMENTS

| | | | | |
|---|---|---|---|---|
| 2006/0241443 | A1* | 10/2006 | Whitmore | ................. A61B 8/08 601/2 |
| 2009/0253986 | A1* | 10/2009 | Frinking | ............. G01S 7/52074 600/431 |
| 2016/0106347 | A1* | 4/2016 | Patwardhan | .......... G06T 7/0012 600/407 |
| 2016/0338664 | A1* | 11/2016 | Misono | ...................... G06T 5/50 |
| 2016/0367225 | A1* | 12/2016 | Ichikawa | ................. A61B 8/14 |
| 2020/0305840 | A1* | 10/2020 | Sboros | ...................... G06T 7/73 |

OTHER PUBLICATIONS

Jensen, Jørgen Arendt, et al. "Ultrasound vector flow imaging—Part I: Sequential systems." IEEE transactions on ultrasonics, ferroelectrics, and frequency control 63.11 (2016): 1704-1721. (Year: 2016).*

* cited by examiner

*Primary Examiner* — Edward F Urban
*Assistant Examiner* — Jongbong Nah
(74) *Attorney, Agent, or Firm* — Dorsey & Whitney LLP (57) ABSTRACT

A method for analyzing a digestive tract of a patient using ultrasound. The method includes receiving a plurality of ultrasound images taken over a time series, determining movement characteristics of objects within the ultrasound images based on movement of one or more pixels in the ultrasound images over the time series, and outputting a visual data that describes the movement characteristics.

20 Claims, 3 Drawing Sheets
(1 of 3 Drawing Sheet(s) Filed in Color)

MOTION ANALYSIS OF THE DIGESTIVE TRACT

CROSS-REFERENCE TO RELATED APPLICATIONS

The present application claims priority under 35 U.S.C. § 119 to U.S. Provisional Application No. 63/079,825 entitled "Motion Analysis of the Digestive Tract," filed on Sep. 17, 2020, which is hereby incorporated by reference herein in its entirety.

FIELD

The present application generally relates to analysis and imaging techniques for anatomical structures, such as the digestive tract.

BACKGROUND

Chronic gastrointestinal (GI) disorders, such as Crohn's disease (CD), cause significant pain and discomfort, and can be debilitating to the point of requiring radical surgical intervention, such as the removal of sections of the bowel. The management of such diseases routinely requires the administration of costly drugs. However, the efficacy of such drugs varies significantly between patients, and an effective drug may become less effective over time. The financial cost of ineffective drugs can be quite large and since GI diseases, such as CD, are often chronic, an ineffective drug may result in far worse outcomes for a patient over the long term. Therefore, it is of considerable interest to be able to assess patients at regular intervals, in order to better target treatment, reduce costs, and improve outcomes.

Currently, many GI disorders are assessed through endoscopy. However, endoscopy is an invasive and costly procedure and preferred for use in the initial diagnosis and monitoring of colonic disease. Other areas of the bowel e.g. the small intestine are often out of reach of the endoscope and less feasible in these cases. Cross sectional imaging (e.g CT and MRI) is routinely used alongside endoscopy not only to assess small bowel disease but also to provide a view of the 'extra-intestinal' manifestations of the disease which are common in Crohn's. Recently, the development of new quantitative image processing techniques for magnetic resonance imaging (MRI) have enabled the non-invasive and quantitative assessment of the GI tract. However, better tolerated and excelling in the assessment of small bowel disease the limited availability of MRI machine time and the limited number of MRI facilities in most healthcare systems mean that regular assessment of the GI health of patients with chronic GI disease such as CD is still prohibitively expensive, as well as being inconvenient for the patient. Furthermore, the COVID-19 pandemic has demonstrated the risks inherent in excessive contact with hospitals for vulnerable patients. Therefore, a technique for assessing GI health which is low-cost, non-invasive, and can in principle be carried out anywhere, is desirable.

SUMMARY

A method for analyzing a digestive tract of a patient is disclosed. The method may include receiving a plurality of ultrasound images taken over a time series, determining movement characteristics of objects within the ultrasound images based on movement of one or more pixels in the ultrasound images over the time series, and outputting a visual data that describes the movement characteristics.

In another embodiment, a system for analyzing a digestive tract is disclosed. The system may include an ultrasound machine including a probe, where the ultrasound machine is configured to capture a plurality of image frames representative of a structure of the digestive tract at different points in time and a processor in electrical communication with the ultrasound machine. The processor is configured to analyze the plurality of image frames to determine motion characteristics of the structure of the digestive tract over the different points in time using movement of one or more pixels of the plurality of image frames over the different points in time and transmit for display a visual output representative of the motion characteristics of the structure.

In another embodiment, one or more non-transitory computer readable media are disclosed. The non-transitory computer readable media are encoded with instructions that, when executed by one or more processors, cause the one or more processors to receive a plurality of ultrasound images of an abdominal area of a patient captured over a time series, select a set of pixels in the plurality of ultrasound images representing an object in the abdominal area of the patient, determine movement characteristics of the object within the plurality of ultrasound images based on movement of the set of pixels in the plurality of ultrasound images, and output a visual data that describes the movement characteristics of the object.

Additional embodiments and features are set forth in part in the description that follows, and will become apparent to those skilled in the art upon examination of the specification and may be learned by the practice of the disclosed subject matter. A further understanding of the nature and advantages of the present disclosure may be realized by reference to the remaining portions of the specification and the drawings, which form a part of this disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The patent or application file contains at least one drawing executed in color. Copies of this patent or patent application publication with color drawing(s) will be provided by the Office upon request and payment of necessary fee.

The description will be more fully understood with reference to the following figures in which components are not drawn to scale, which are presented as various examples of the present disclosure and should not be construed as a complete recitation of the scope of the disclosure, characterized in that.

DETAILED DESCRIPTION

The present disclosure is directed to utilizing and analyzing ultrasound images to detect characteristics of anatomical structures, such as a patient's digestive tract, in order to diagnosis, treat, and evaluate various conditions, drug efficacy, and diseases. Ultrasound is a safe, portable, and versatile medical imaging modality used extensively across all health verticals. However, to date, its use in GI assessment has been limited by the need for direct interpretation by highly trained abdominal ultrasound specialists, such as consultant radiologists or specially trained gastroenterologists. These interpretations are rapid, but are qualitative rather than quantitative, meaning there is no established technique to directly compare the health of the GI tract between different ultrasound examinations beyond measuring bowel wall thickness. Additionally, unlike MRI, the images obtained through ultrasound scanning are highly operator dependent. Such variability adds an additional layer of complexity to the comparison of ultrasound examinations, as variations in operator competence, equipment, settings, viewports, and patient preparation, confound attempts to gain a clear picture of the patients GI health at a given point in time. As described herein, the system and methods allow annotation and analysis of ultrasound images and may include quantitative biomarkers for GI health, disease progression, at various points within the images, as well as to summarize the overall GI health and/or disease progression with one or more quantitative scores, that can be consistently applied across examinations, regardless of variations in variables such as operator competency, equipment, settings, viewport, and patient preparation.

For example, the system may include an ultrasound machine and a computing system in communication with the ultrasound machine. The ultrasound machine is used to capture a series of images, e.g., time series, of the target area of the patient, such as the abdomen for evaluation of the digestive tract. The image series or image frames are evaluated to determine motion of pixels between frames such that a vector flow map of pixel movement across the image series can be generated. Filtering can be applied to remove noise and other unwanted data (e.g., movement due to breathing of the patient, probe motion, or the like). The system may then output various data that describes clinically relevant motion, such as the gut motility, as well as biomarkers determined from the data. By comparing data of the same patient over time (e.g., every two weeks, every few days, before and after administration of a treatment, etc.), the patient's GI health, disease progression, drug efficacy, and the like may be determined. As another example, the system may be used in clinical studies to compare results of different patients or patient groups.

Conventional techniques have not utilized ultrasound images to assess deformation or movement of the digestive tract. The digestive tract can be variable over time, resulting in inconsistency across images, as well as the deficiencies noted above that are inherent to ultrasound data collection generally. As such, the present techniques allow a cheap, fast, and easy diagnostic tool to be utilized for a new area of clinical evaluation and treatment, and help to remove the inherent noise and other variables in data collective via ultrasound.

Figure 1:
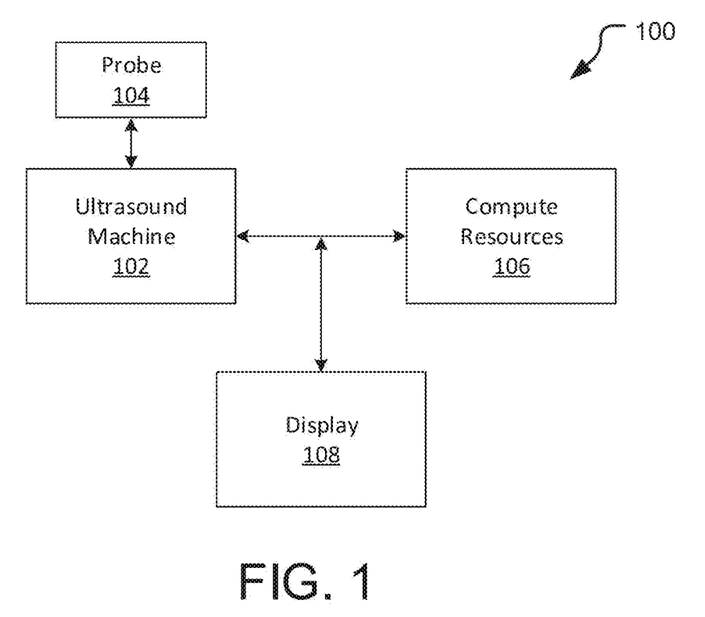
FIG. 1 is a block diagram of a system for analyzing anatomical motion via ultrasound.

Turning to the figures, a system for detecting and evaluating motion of a user's internal anatomy will be discussed in more detail. FIG. 1 illustrates a system 100 including an ultrasound machine 102, a probe 104, one or more compute resources 106, and optionally a display 108. The various components of the system 100 may be in direct communication and/or indirect communication. In some instances, the compute resources 106 and/or display 108 may be separate components from the ultrasound machine 102 or may be integrated with the ultrasound machine 102. Similarly, the compute resources 106 and/or display 108 may be in communication with the ultrasound machine 102 via wireless or wired means, including one or more networks, as needed. In one example, many of the compute operations described herein may be done locally, but in other examples, some operations may be in done remotely, such as on one or more cloud resources or the like.

The ultrasound machine 102 may be generally any type of component configured to generate and capture ultrasound acoustic or sound waves, e.g., those with frequencies above the upper limit of human hearing or in the ultrasound range. For example, the ultrasound machine 102 may include a probe 104 that applies pulses of ultrasound waves into tissue, then as the pulses echo from the tissue, captures the reflected waves. In this manner, the ultrasound machine 102 can generate data or images of the tissue (e.g., reflection properties of the tissue). In some embodiments, the ultrasound machine 102 is used to generate images, such as B-mode or brightness images, that display the acoustic impedance of a two-dimensional cross-section of tissue. In some embodiments, a 3D ultrasound imaging system may be employed, which builds a 3D picture of the relevant anatomy by either registering a stack of cross-sectional 2D images, or using a probe which features a 2D array. The techniques described may be extended to work with 3D ultrasound data and/or other sensing modalities, such as, but not limited to, elastography or the like. Often, the ultrasound machine 102 will generate beamformed images that include at least some directional aspect.

The probe 104 may be dependent on the type of ultrasound machine 102, but generally is any type of transducer that generates and captures sound waves. In some embodiments, the probe 104 may be shaped based on the desired anatomical area to be scanned, e.g., the probe 104 may be curvilinear for scanning the abdominal area of a patient.

The compute resource 106 is any type of computing device, such as, but not limited to, a computer, server, processor, processing elements, or the like. In some embodiments, the compute resource 106 or computer, may be a standalone device that receives data from the ultrasound machine 102 or probe 104. However, in other embodiments, features of the compute resource 106 may be integrated directly into the ultrasound machine 102, such as to allow a more compact system 100. The compute resources 106 are configured to analyze the images or other data captured by the ultrasound machine 102 in order to generate output data corresponding to movement and/or other characteristics of the scanned area of the patient. For example, the compute resources 106 can generate movement data that can be displayed, e.g., via display 108, to a clinician, doctor, nurse, patient, or the like, that describes the movement of the anatomical structure.

Figure 4:
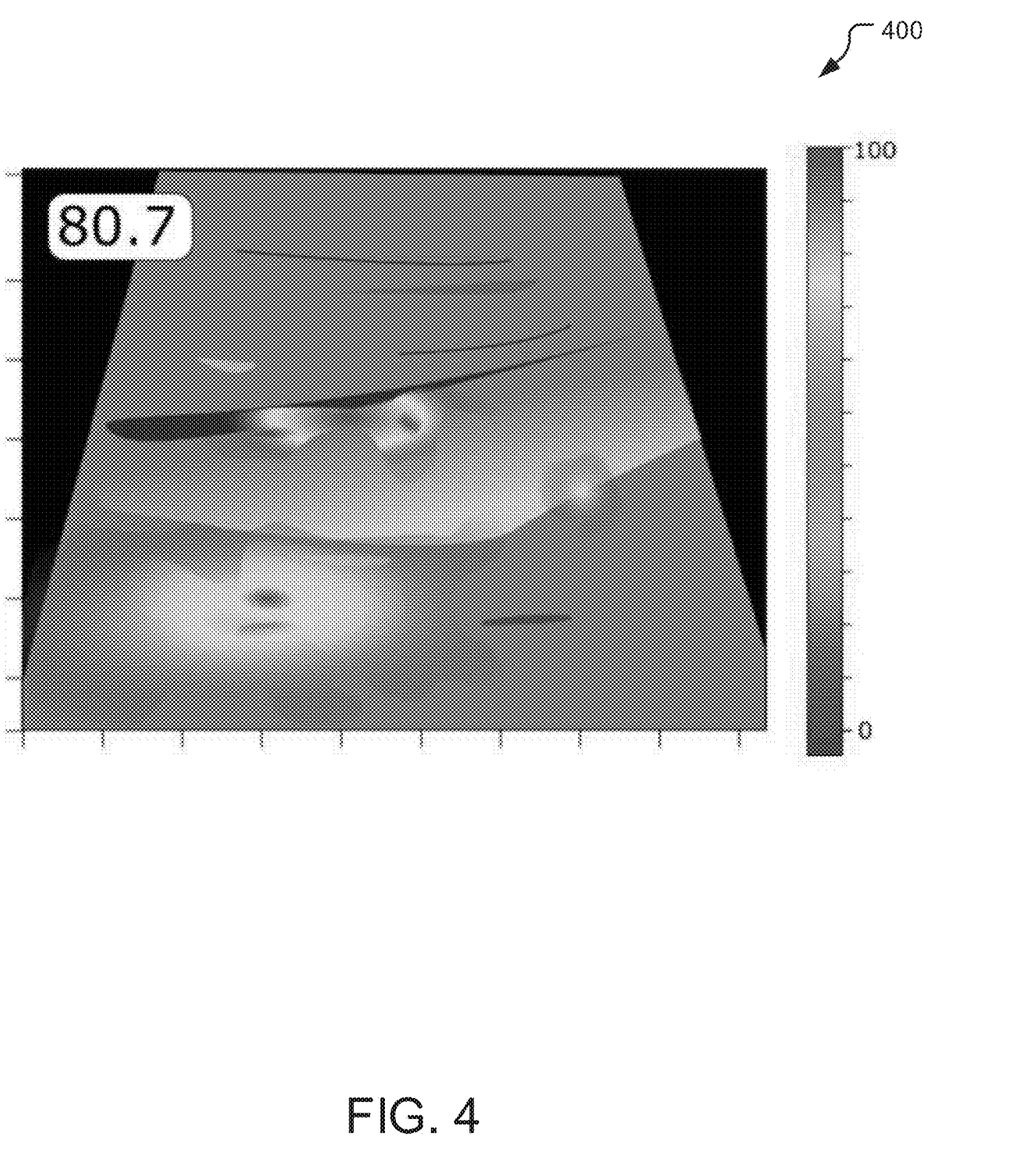
FIG. 4 is a sample image of an illustrative ultrasound frame with output data in the form of a heat or color coded map overlaid thereon.

The display 108 may be connected to one or both of the ultrasound machine 102 or the compute resource 106 (either directly or indirectly) and is substantially any type of device that can generate a visual image or other output. For example, the display 108 may be configured to display images captured by the ultrasound machine 102, as well as overlay or other data generated by the compute resource 106, such as, but not limited to, movement maps, tables, summary maps, time series overlay images, vector information, or the like. Examples of the data displayed or output by the display 108 are shown in FIG. 4, illustrating a color-coded map overlaid on the ultrasound frame, with the different colors corresponding to different movement information. In some instances, the display 108 may also include other types of output to a user, such as audio and/or haptic outputs.

Figure 2:
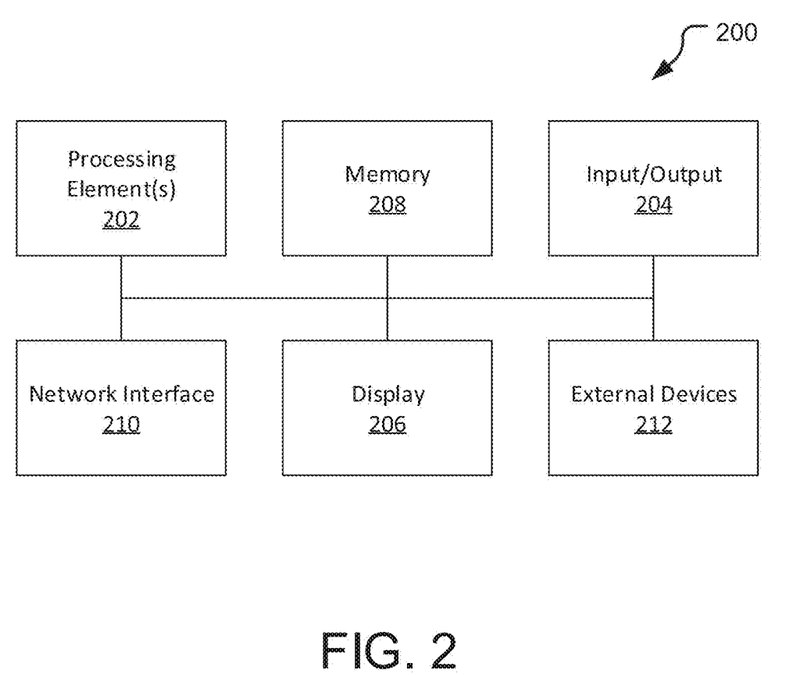
FIG. 2 is a schematic diagram of an example computer system implementing various embodiments of the examples described herein.

It should be noted that the various components of the system 100 may be implemented on one or more computing devices. FIG. 2 is a schematic diagram of an example computer system 200 for implementing various embodiments in the examples described herein. The computer system 200 (or select components thereof) may be used to implement the compute resource 106, ultrasound machine 102, and/or display 108. The computer system 200 is used to implement or execute one or more of the components or operations disclosed herein, e.g., the method 300. The computer system 200 may include one or more processing elements 202, an input/output interface 204, a display 206, one or more memory components 208, a network interface 610, and one or more external devices 212. Each of the various components may be in communication with one another through one or more buses, communication networks, such as wired or wireless networks.

The processing element 202 may be any type of electronic device capable of processing, receiving, and/or transmitting instructions. For example, the processing element 202 may be a central processing unit, microprocessor, processor, or microcontroller. Additionally, it should be noted that some components of the computer 200 may be controlled by a first processor and other components may be controlled by a second processor, where the first and second processors may or may not be in communication with each other.

The memory components 208 are used by the computer 200 to store instructions for the processing element 202, as well as store data, such as the output data from the compute resources 106 and/or ultrasound machine 102 and the like. The memory components 208 may be, for example, magneto-optical storage, read-only memory, random access memory, erasable programmable memory, non-transitory memory, flash memory, or a combination of one or more types of memory components.

The display 206 provides visual feedback to a user. The display 206 may be the same or similar to the display 108, but in some instances the various devices may have displays that are separate from the system display 108. Optionally, the display 206 may act as an input element to enable a user to control, manipulate, and calibrate various components of the compute resources 106 and/or ultrasound machine 102 described in the present disclosure. The display 206 may be a liquid crystal display, plasma display, organic light-emitting diode display, and/or other suitable display. In embodiments where the display 206 is used as an input, the display may include one or more touch or input sensors, such as capacitive touch sensors, a resistive grid, or the like.

The I/O interface 204 allows a user to enter data into the computer 200 (or a peripheral device, such as a smartphone, coupled to the computer 200), as well as provides an input/output for the computer 200 to communicate with other devices or services. The I/O interface 204 can include one or more input buttons, keyboards, touch pads, and so on.

The network interface 210 provides communication to and from the computer 200 to other devices. The network interface 210 includes one or more communication protocols, such as, but not limited to Wi-Fi, Ethernet, Bluetooth, and so on. The network interface 210 may also include one or more hardwired components, such as a Universal Serial Bus (USB) cable, or the like. The configuration of the network interface 210 depends on the types of communication desired and may be modified to communicate via Wi-Fi, Bluetooth, and so on.

The external devices 212 are one or more devices that can be used to provide various inputs to the computing device 200, e.g., mouse, microphone, keyboard, trackpad, or the like. The external devices 212 may be local or remote and may vary as desired. In some examples, the external devices 212 may also include one or more additional sensors.

Figure 3:
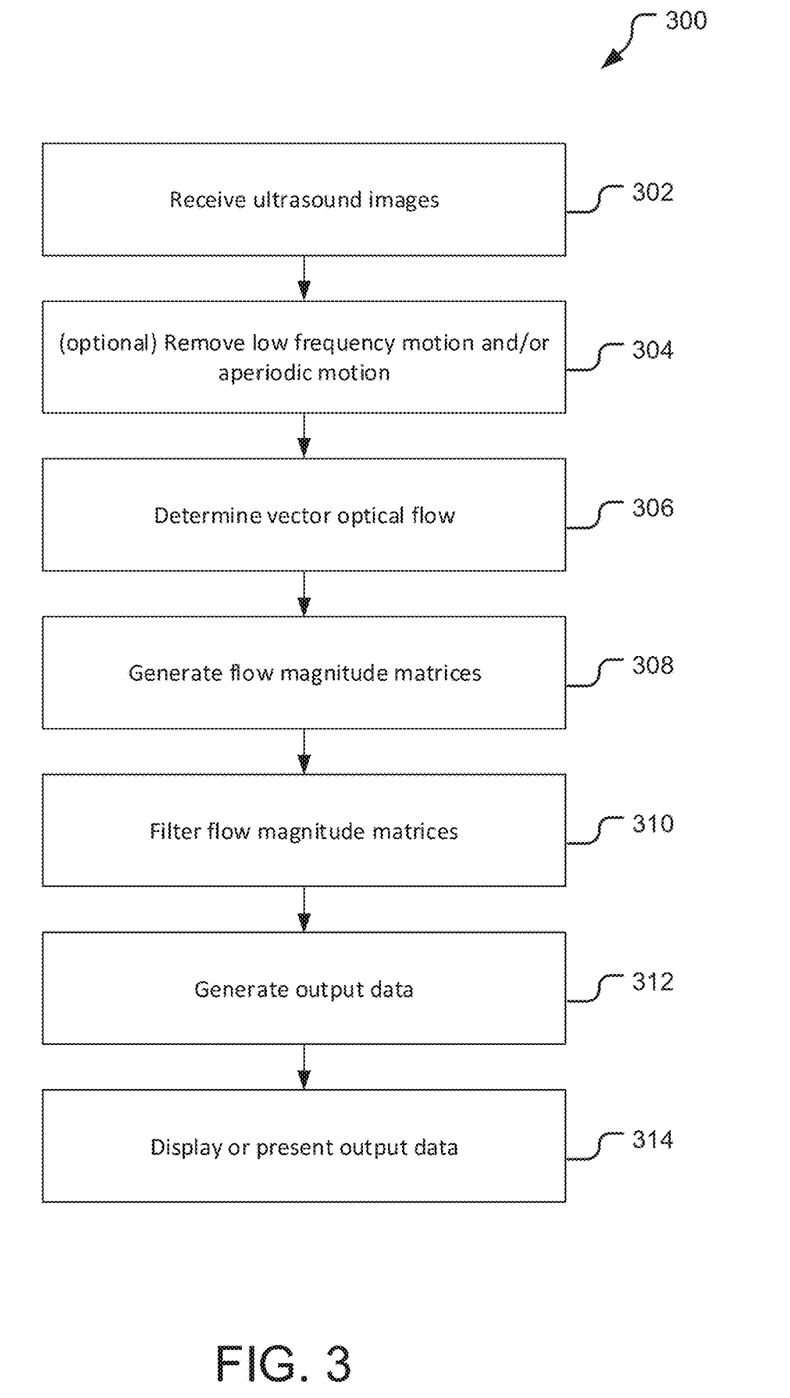
FIG. 3 is a flow chart illustrating a method for analyzing anatomical motion using the system of FIG. 1.

Turning to FIG. 3, a method 300 of utilizing the system 100 for capturing and analyzing motion of anatomical structures of a patient will now be discussed. The method 300 may begin with operation 302 and one or more ultrasound images are received. For example, the ultrasound machine 102 and probe 104 may be used to scan the patient and generate image frames across a time period, e.g., time series of images. The patient may be prepped before the scan, such as with food, drugs, contrast agents, and/or fasting, depending on the anatomical characteristics to be observed. In various instances, the images may be collected as a trained operator, such as a radiologist or sonographer, or an untrained operator (e.g., patient) with a guidance system, scans the anatomical area with the probe 104. The probe 104 generates ultrasounds and directs them towards the desired area of the patient (e.g., abdominal area) and captures the reflected sound waves after the waves have reflected from the internal structures of the patient.

The ultrasound machine 102 captures and stores the images of the internal structures. In some instances, contrast, depth, gain, and brightness settings may be adjusted (e.g., through manual control or by an automatic calibration program) to optimize the visibility of the desired anatomical detail. Similarly, on-line image stabilization systems may be used as well.

In one embodiment, the images may be B-mode images that are beamformed, and be captured at a generally high frame rate, e.g., 10 frames per second. The optimal frame rate may be determined by balancing resolution, viewport size and cost considerations, although higher frame rates are generally advantageous for this technique. For example, utilizing 10 frames per second allows the system to have sufficiently clear resolution to identify features in the images. However, in other instances, where resolution may not be as important, the frame rate can be increased as desired.

In some embodiments, it should be noted that the method may not be driven by capturing a particular number of frames for analysis, but rather, the duration and visualization of a contraction or other desired GI movement. For example, during the scan, the operator or clinician may determine that a bowel contraction has been detected and captured the desired data within a short time period, in which case the scan may termination with only a small number of frames. However, in other embodiments, the desired movement may not be captured and a longer scan time may be needed. As such, the scan duration and number of captured frames for any given instance may vary and the longer the scan the more images are captured. In various instances, the scan length may range from about 5 to 20 seconds, where one image is captured per second. However, the frame rate and scan length are variable and may be adjusted as needed, as such the discussion of any particular rate and time is meant as illustrative only.

The beamforming may be done by the ultrasound machine 102 and/or at a later stage by the compute resources 106 and provides directional information from the received ultrasound data from the probe 104. For example, the probe 104 may be configured to emit beamformed signals in order to provide spatial information in the reflected information. Beamforming may be used to render images from sound waves and convert radio frequency (RF) and/or quadrature detection (IQ) data to images and in these instances, the images, rather than the raw data may be the basis for the analysis. However, other types of ultrasound data, including the raw RF and IQ data, and frame rates may be used to capture the patient images.

In embodiments where the system 100 is used to analyze the GI tract, the view of the terminal ileum (TI) may be captured by the probe 104, such as by the operator aligning the probe 104 with an exterior of the patient that corresponds to a location of the TI or is otherwise configured to capture reflections from the TI. Additionally, in some instances, the operator may compress the probe 104 into the tissue of the patient, e.g., into the abdomen in order to capture images of the TI in response to mechanical stimuli.

The detected image information from the ultrasound machine 102 may then be provided to the compute resources 106. In this manner, the compute resources 106 may receive images from the ultrasound sound machine 102. The images may be captured at different times that may be sequential, such as a time series of frames captured at different points in time. For example, these may be multiple frames captured and transmitted to the compute resources 106 during a series of seconds. The number of frames captured may be determined based on the clinical need, e.g., some patients may need more images captured than others based on diagnosis, bowel movement during examination, probe steadiness, length of time that patient can hold his or her breath if needed, and so on.

It should be noted that the system 100 may be configured such that all images captured by the ultrasound machine 102 are transferred to the compute resources 106 for analysis. Alternatively, a subset of images may be transferred, e.g., an operator may provide an input, such as via selecting a button or icon on the ultrasound machine 102, that initiates the capture, transfer, and/or storage of images for analysis by the compute resources 106. In these embodiments, the data transfer to the compute resources 106 may be smaller and limited to when the probe 104 is positioned in the desired area, removing irrelevant analysis and the like. However, as noted below, the processing operations can remove such irrelevant or undesired data as well. In instances where the images are not immediately transferred to the compute resources 106, the images may optionally be stored, e.g., on local memory of the ultrasound machine 102 or another storage element, such as a server. Illustrative formats include a digital imaging and communications in medicine (DICOM) file or on a picture archiving and communication system (PACS) server.

With reference again to FIG. 3, once the compute resources 106 receive one or more images, the method 300 may proceed to operation 304. In operation 304, noise, such as low frequency motion and/or aperiodic motion (e.g., arising from involuntary probe 104 motion during capture, patient breathing, etc.), may be filtered from the images. For example, Sources of motion in the frames may be due to probe movement, respiratory cycle, and/or subject movement, all of which may present as movement data, but are not due to the movement of the GI tract. In many embodiments, these motion sources can be managed through careful instruction of the subject and operator training for use of the probe (e.g., subject can hold his or her breath during portions of the examination and reduce physical movement, and/or clinician can learn steady probe usage).

In some instances where such movement cannot be eliminated, an automated image compensation operation may be utilized to identify and correct for sources of motion attributed to external motion sources. An image compensation operation may utilize an algorithm based on robust component analysis (RPCA), described, for example, by Hamy et al. (2014). The algorithm may represent a given ultrasound cine clip as a matrix M whereby each column contains the pixels for a particular time-frame. This matrix may be decomposed into low-rank (L) and sparse (S) matrices, by applying an optimization algorithm which minimizes $\|L\|_* + \lambda\|S\|_1$ (where the * and 1 subscripts represent the nuclear and $l_1$ norms respectively and $\lambda$ is a trade-off parameter) subject to the constraint L+S=M. Starting with a $\lambda$ value of $1/\sqrt{N_p}$, where $N_p$ is the number of pixels in each frame, or alternatively any other suitable value, a respiratory-motion corrected ultrasound cine loop which preserves motility information may be obtained by iteratively deforming the cine clip encoded in the original matrix M according to the computed deformation fields which register each frame of the cine clip encoded in L to the preceding frame. One such registration algorithm which may be used is given by Myronenko and Song (2010). The maximum value of $\lambda$ and the amount by which $\lambda$ is incremented on each iteration may be determined such that all of the respiratory motion is removed whilst preserving peristaltic bowel motion (motility). In this manner, the time series data captured may be pre-processed to remove the non-motility data. In these embodiments, the reduction of noise during data capture or the scan and optionally preprocessing may help to increase the quality of the data.

With reference to FIG. 3, after operation 304, the method 300 may proceed to operation 306 and a vector optical flow may be determined by the compute resources 106. For example, images within the plurality of received images, e.g., image frames within a time series, are analyzed to determine a vector optical flow for various pixels in the images. As a specific example, a pixel in a first image is identified and then changes in that pixel over the frames or time series, are determined. One algorithm for determining dense optical flow is given by Farnebäck, which may be summarized as follows: for two consecutive frames of ultrasound pixel values $f_1(x)$ $f_2(x)$ where x refers to a point in some local coordinate system, the flow at each point in the image may be found by computing $$d(x) = \left(\sum_i w(x_i)A(x_i)^T A(x_i)\right)^{-1} \sum_i w(x_i)A(x_i)b(x_i)$$

where A is a matrix, b is a vector, and w is a scalar weighting function. The sum is performed over a set of points $x_i$ which define a sub-region of the image. The initial values of A and b are computed by fitting a second-order polynomial to the pixel values of the first and second frames. The algorithm may be performed iteratively, first calculating d(x) by summing over the entire image, and then using this information to refine A and b. The equation can then be iteratively applied to successively smaller areas of the image, to find a vector flow field defined at each pixel. Various parameters can be tuned to optimize the algorithm for particular types of motion, such as the weighting function w, the number of iterations, the size of the area for each stage of the algorithm, and the parametrization of d(x). Further details can be found in Farnebäck et. al. In one embodiment, parameters for the optical flow as discussed above are selected to ensure that the analysis captures physiological motion relevant to the clinical application (e.g., relevant to the desired areas and focus of the scan), e.g., the various parameters can be scaled based on the desired clinical operation. In operation 306, vectors defining movement of image information across the time series or analyzed image frames may be determined.

In operation 308, the compute resources 106 may generate one or more matrices of flow magnitudes, e.g., the magnitude of a vector at each point. For example, for the various images or frames in the time series, a matrix of flow magnitudes may be computed for each pixel or select pixels in the images. The magnitude of the flow at a given point in the picture is given by $$M(x) = \sqrt{f_x(x)^2 + f_y(x)^2}$$

where x is a point within the vector flow field, and $f_x$ and $f_y$ are the horizontal and vertical components of the vector flow field respectively.

In operation 310, the compute resources 106 may filter the flow magnitude matrices. For example, the matrices may be digitally filtered in the time domain using an impulse response function that favors physiologically relevant motion and discards motion caused by movement of the probe 104, breathing, and other visual artifacts. An IR filter may be implemented as follows: each pixel of the ultrasound time series may be considered as a discrete 1D time series $x_t$. The IR filter is defined by two sets of numbers $a_t$ and $b_t$. The filtered time series $y_t$ is computed by the equation $$y_t = \frac{1}{a_0}\left(\sum_{i=0}^{i=t} b_i x_{t-i} - \sum_{j=1}^{j=t} a_j x_{t-j}\right).$$

The values for $a_t$ and $b_t$ may be given by periodic sampling of some analytic function, such as $$a(t) = 1$$

$$b(t) = \exp[t^2/\varphi]$$

where φ is a tunable parameter. This particular IR filter has the effect of making signals indicating motion more persistent, drawing the eye to those regions. However, other types of digital filters, such as those in the time domain, may be used as well and the above IR filter is just one example.

In operation 312, the compute resources 106 generate output data. The type and format of the output data may be varied depending on the type of information requested or preferred by the clinician, patient or the like. In some embodiments multiple data outputs may be generated as well.

In a first example, a first data output may be generated that may include two or more matrices (e.g., a first matrix for the x axis and a second matrix for the y axis) that contains the vector flow data for frames within the time series images. In a second example, a data output may be generated that includes a matrix having the scalar flow data for frames within the time series of images. In a third example, a vector (e.g., length of one) may be generated from all or a specified sub-region of the matrices from the first and second data outputs for frames within the time series of frames. As a fourth example, a vector (e.g., length of one) of summary statistics may be generated that includes all or a specified sub-region of all or a specified sub-sequence of matrices. The selection of sub-regions and sub-sequences for the data outputs may be specified during examination, e.g., using an interactive input that provides a user input to the system 100 and/or as a user prompt or user input during the analysis operations. Alternatively or additionally, an algorithm may be used to select sub-regions and sub-sequences automatically, such as based on detected motion characteristics, formed areas detected in the images, or the like. The selection of sub-regions and sub-sets may be used to help ensure that certain data outputs (e.g., third and fourth examples) may take into account only desired areas of data, e.g., only the clinically relevant aspects of the ultrasound scan.

It should be noted that the data output generated in operation 312 may be displayed on the display 108, e.g., as a real-time overlay of the ultrasound images during examination or the scan and/or may be presented as a digital report. It should be noted that real-time display may encompass a sufficiently low latency that the operator or clinician can respond to the presented data and adjust the probe as needed. As one example, the system may be configured to have a 1 frame delay, where times series data is used to up to a particular point in time at which point the most recent data and calculations are transmitted for display, where the lag may be due to just processing. In another example, the real-time data presented may include data up to a particular frame but not include future frames. Depending on the desired latency reduction, filtering (e.g., to remove motion due to breathing or other non-GI tract movement) may not be removed for the real-time display. In general, the present system may have a latency limited by the reflections of the ultrasound probe and so may be considered real-time relative to the display of the ultrasound images. In other embodiments, the operator may collect the data and the analysis and overlay may be done after the data collection is complete and replayed as a video or other display.

With reference again to FIG. 3, in operation 314, data may be presented to the user (e.g., clinician, doctor, patient, or the like). The data may be presented dynamically and in real-time during the scan, such as on the display 108 and/or may be presented at a different point in time.

As a first example, the data may be presented as an overlay of time-series information over the ultrasound images, e.g., a color map may be overlaid on the ultrasound image series image data. As a second example, one or more summary maps may be generated, e.g., a color map may be overlaid on top of a representative image of the target anatomy, such as select image from the time series images and/or an image that is generated from the time series data or images. As a third example, a time series vector, such as a length of one, may be overlaid, e.g., a list of numbers may be overlaid on top of the ultrasound time series data, or a graphical representation of the vectors (e.g., bar chart, virtual gauge, or other visual system) may be overlaid. As another example, the data may be presented as lines or other marks on a one-dimensional chart with the x-axis representing time. As a fourth example, a summary statistic vector, such as a table of numbers, may be generated.

FIG. 4 illustrates an example of an output image overlaid on an ultrasound output, such as an ultrasound image frame. As shown in FIG. 4, the different colored areas illustrate different movement of the area. For example, one color (e.g., red) may represent a larger magnitude of movement as compared to another color (e.g., blue), with shades between the two representing variations along the scale. As another example, a color scale may be used to illustrate acceleration and/or displacement. The type of movement or output characteristic may be varied based on the clinical needs, ultrasound images, or the like.

The foregoing description has a broad application. For example, while examples disclosed herein may focus on scans of the digestive tract, it should be appreciated that the concepts disclosed herein may equally apply to other anatomical structures. Accordingly, the disclosure is meant only to provide examples of various systems and methods and is not intended to suggest that the scope of the disclosure, including the claims, is limited to these examples.

The technology described herein may be implemented as logical operations and/or modules in one or more systems. The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method for analyzing a digestive tract of a patient comprising:
   receiving a plurality of brightness beamformed ultrasound images representative of a structure of the digestive tract taken over a time series;
   determining movement characteristics of the structure of the digestive tract based on movement of one or more pixels in the plurality of brightness beamformed ultrasound images over the time series comprising:
      determining a vector optical flow for the one or more pixels in the plurality of brightness beamformed ultrasound images through algorithmic image analysis of the one or more pixels; and
      generating a flow magnitude matrix for the vector optical flow; and
   outputting a visual data that describes the movement characteristics.

2. The method of claim 1, wherein determining the movement characteristics further comprises:
   applying a respiratory motion correction algorithm prior to determining optical flow.

3. The method of claim 1, wherein determining the movement characteristics further comprise:
   filtering the flow magnitude matrix.

4. The method of claim 1, wherein the visual data comprises an overlay of movement data on a ultrasound image.

5. The method of claim 1, wherein the outputting the visual data is done in real-time while the plurality of ultrasound images are captured.

6. The method of claim 1, wherein the visual data comprises one or more of: a color map, a movement vector, or a summary statistics vector.

7. A system for analyzing a digestive tract comprising:
   an ultrasound machine including a probe, wherein the ultrasound machine is configured to capture a plurality of image frames representative of a structure of the digestive tract at different points in time; and
   a processor in electrical communication with the ultrasound machine, wherein the processor is configured to:
      analyze the plurality of image frames to determine motion characteristics of the structure of the digestive tract over the different points in time using movement of one or more pixels of the plurality of image frames over the different points in time; and
      transmit for display a visual output representative of the motion characteristics of the structure.

8. The system of claim 7, wherein the image frames are captured as brightness beamformed images.

9. The system of claim 7, wherein to analyze the plurality of image frames, the processor is further configured to:
   determine a vector optical flow for the one or more pixels within the image frames over the different points in time; and
   generate a plurality of flow magnitude matrices based on the vector optical flow.

10. The system of claim 9, wherein to analyze the plurality of image frames, the processor is further configured to:
    apply a respiratory motion correction algorithm prior to determining the vector optical flow of the one or more pixels within the image frames.

11. The system of claim 9, wherein to analyze the plurality of image frames, the processor is further configured to:
    filter the flow magnitude matrices.

12. The system of claim 7, wherein the processor is further configured to output the visual data as the image frames are captured.

13. One or more non-transitory computer readable media encoded with instructions that, when executed by one or more processors, cause the one or more processors to:
    receive a plurality of ultrasound images of an abdominal area of a patient, the plurality of images captured over a time series;
    select a set of pixels in the plurality of ultrasound images, the set of pixels representing a structure of a digestive tract in the abdominal area of the patient;
    determine movement characteristics of the structure of the digestive tract within the plurality of ultrasound images based on movement of the set of pixels in the plurality of ultrasound images; and
    output a visual data that describes the movement characteristics of the structure of the digestive tract.

14. The non-transitory computer readable media of claim 13, wherein the movement of the set of pixels is a vector optical flow for the set of pixels, wherein the instructions further cause the one or more processors to:

generate a flow magnitude matrix for the vector optical flow.

15. The non-transitory computer readable media of claim 14, wherein the instructions further cause the one or more processors, when determining the movement characteristics of the object, to:

apply a respiratory motion correction algorithm prior to determining optical flow.

16. The non-transitory computer readable media of claim 13, wherein the instructions further cause the one or more processors, when determining the movement characteristics of the object, to:

filter the flow magnitude matrix.

17. The non-transitory computer readable media of claim 13, wherein the visual data comprises an overlay of movement data on an ultrasound image.

18. The non-transitory computer readable media of claim 13, wherein the ultrasound images are brightness beam-formed images.

19. The method of claim 1, wherein the algorithmic image analysis comprises a Farnebäck algorithm.

20. The system of claim 9, wherein the vector optical flow is determined through a Farnebäck algorithm.

* * * * *